United States Patent

Merriam

[11] Patent Number: 5,965,828
[45] Date of Patent: *Oct. 12, 1999

[54] FLUID HANDLER AND METHOD OF HANDLING A FLUID

[75] Inventor: Richard Merriam, Dallas, Tex.

[73] Assignee: Abbott Laboratories, Abbott Park, Ill.

[ * ] Notice: This patent is subject to a terminal disclaimer.

[21] Appl. No.: 08/862,092

[22] Filed: May 22, 1997

Related U.S. Application Data

[63] Continuation-in-part of application No. 08/572,835, Dec. 14, 1995, Pat. No. 5,723,795.

[51] Int. Cl.$^6$ .................................................. G01N 35/10
[52] U.S. Cl. ............................................. 73/863; 137/557
[58] Field of Search ................................. 73/863, 864.11, 73/864.12, 864.22, 864.24, 863.02, 863.03, 864.25; 137/1, 557; 222/23; 141/94

[56] References Cited

U.S. PATENT DOCUMENTS

| | | | |
|---|---|---|---|
| 2,986,924 | 6/1961 | Becker | 73/37.5 |
| 3,283,565 | 11/1966 | Muller et al. . | |
| 3,415,268 | 12/1968 | Tweed | 137/209 |
| 3,444,737 | 5/1969 | Jago . | |
| 3,474,902 | 10/1969 | Putman | 209/1 |
| 3,494,191 | 2/1970 | Cawley et al. . | |
| 3,661,191 | 5/1972 | Harley et al. | 141/41 |
| 3,712,136 | 1/1973 | Monsen | 73/298 X |
| 3,735,636 | 5/1973 | Burke | 73/290 R |
| 3,754,444 | 8/1973 | Ure et al. . | |
| 3,900,290 | 8/1975 | Hornstra . | |

(List continued on next page.)

FOREIGN PATENT DOCUMENTS

| | | |
|---|---|---|
| 0052355 | 5/1982 | European Pat. Off. . |
| 0169071 | 1/1986 | European Pat. Off. . |
| 0215534 | 3/1987 | European Pat. Off. . |
| 0273128 | 7/1988 | European Pat. Off. . |
| 0341438 | 11/1989 | European Pat. Off. . |
| 0199466 B1 | 8/1990 | European Pat. Off. . |
| 0438136 | 7/1991 | European Pat. Off. . |
| 0223751 | 10/1991 | European Pat. Off. . |

(List continued on next page.)

OTHER PUBLICATIONS

Patent Abstracts of Japan Grp P590, vol. 11, No. 201 Abs pub date Jun. 30, 1987 (62–24151) "Suction Discharger for Automatic Chemical Analyzer".

Patent Abstracts of Europe (DE–4241822 A1) Jun. 16, 1994 Error detector circuit for evaluator of sensor signals –detects when sensor signal enters one of two defined error signals using bridge circuit, and receives signals via A to D converter.

A Simple Capillary Viscometer, C. Bowlt; Physics Education, vol. 10; No. 2, pp. 102–103 Mar. 1975.

A Highly Sensitive Immunoenzymometric Assay Involving "Common–Capture" Particles And Membrane Filtration J. Kang, et al.; Clin Chem 32/9, 1682–1686(1986) month not give.

Abbott Prism: A Multichannel Heterogenous Chemiluminescence Immunoassay Analyzer, O. S. Khalil, *Clin Chem.* 37/9, 1540–1547 (1991), month not given.

(List continued on next page.)

*Primary Examiner*—Thomas P. Noland
*Attorney, Agent, or Firm*—Mark C. Bach

[57] ABSTRACT

Methods of fluid handling are disclosed. In one method, a nozzle is moved adjacent a container for a fluid. A pump fluidly associated with the nozzle is energized to move fluid with respect to the nozzle. A pressure transducer fluidly associated with the nozzle is energized to monitor transient pressure fluidly associated with the nozzle. The transient pressure fluidly associated with the nozzle is substantially continuously monitored with the pressure transducer at least during operation of the pump. It is determined whether movement of fluid with respect to the nozzle is intended or unintended based on the substantially continuously monitored pressure fluidly associated with the nozzle.

4 Claims, 5 Drawing Sheets

U.S. PATENT DOCUMENTS

| | | | |
|---|---|---|---|
| 3,903,840 | 9/1975 | Gemelli | 118/712 |
| 3,972,614 | 8/1976 | Johansen et al. | 356/36 |
| 3,976,989 | 8/1976 | Smith | 137/552.7 X |
| 3,992,158 | 11/1976 | Przybylowicz et al. | |
| 4,030,888 | 6/1977 | Yamamoto et al. | 356/39 X |
| 4,041,995 | 8/1977 | Columbus | 141/275 |
| 4,053,381 | 10/1977 | Hamblen et al. | |
| 4,056,982 | 11/1977 | Jones . | |
| 4,072,934 | 2/1978 | Hiller et al. | 141/7 X |
| 4,083,363 | 4/1978 | Philpot, Jr. | 73/54.07 X |
| 4,090,129 | 5/1978 | Gear . | |
| 4,093,849 | 6/1978 | Baxter, Jr. et al. | 235/92 PC |
| 4,103,229 | 7/1978 | Gear . | |
| 4,117,727 | 10/1978 | Friswell et al. | |
| 4,140,018 | 2/1979 | Maldarelli et al. | |
| 4,157,498 | 6/1979 | Johnson . | |
| 4,160,373 | 7/1979 | Fastaia et al. | 340/608 X |
| 4,161,188 | 7/1979 | Jorgensen | 137/386 |
| 4,165,484 | 8/1979 | Haynes . | |
| 4,211,249 | 7/1980 | Richards | 137/393 |
| 4,218,610 | 8/1980 | Baxter, Jr. et al. | 235/92 PC |
| 4,228,831 | 10/1980 | Kerns | 141/27 |
| 4,241,606 | 12/1980 | Vandenhoeck | 73/290 R |
| 4,258,001 | 3/1981 | Pierce et al. | 422/56 |
| 4,287,155 | 9/1981 | Tersteeg et al. | 422/64 |
| 4,340,390 | 7/1982 | Collins et al. | 141/130 X |
| 4,410,109 | 10/1983 | Murrell, Jr. et al. | 222/52 |
| 4,452,899 | 6/1984 | Alston | 436/46 |
| 4,515,178 | 5/1985 | Campau | 137/393 |
| 4,555,957 | 12/1985 | Frankel et al. | 73/864.14 |
| 4,586,546 | 5/1986 | Mezei et al. | 141/18 |
| 4,591,568 | 5/1986 | Banno et al. | 436/180 |
| 4,606,703 | 8/1986 | Baines | 417/86 |
| 4,623,461 | 11/1986 | Hossom et al. | 210/445 |
| 4,652,533 | 3/1987 | Jolley | 436/518 |
| 4,662,540 | 5/1987 | Schroter | 222/55 |
| 4,668,948 | 5/1987 | Merkel | 73/37 X |
| 4,671,123 | 6/1987 | Magnussen, Jr. et al. | 73/864.16 |
| 4,675,301 | 6/1987 | Charneski et al. | 436/180 |
| 4,696,183 | 9/1987 | Mitsumaki et al. | 73/863.01 X |
| 4,710,163 | 12/1987 | Butterfield | 604/65 |
| 4,715,413 | 12/1987 | Backlund et al. | 141/94 |
| 4,729,876 | 3/1988 | Hennessy et al. | 422/103 |
| 4,736,638 | 4/1988 | Okawa et al. | 73/864.24 |
| 4,743,228 | 5/1988 | Butterfield | 604/50 |
| 4,777,832 | 10/1988 | Prodosmo et al. | 73/863.02 |
| 4,780,833 | 10/1988 | Atake | 364/509 |
| 4,794,085 | 12/1988 | Jessop et al. | 436/54 |
| 4,803,050 | 2/1989 | Mack | 422/65 |
| 4,846,003 | 7/1989 | Marquiss | 73/864.24 |
| 4,864,856 | 9/1989 | Ichikawa et al. | 73/290 |
| 4,893,515 | 1/1990 | Uchida | 73/864.34 |
| 4,944,922 | 7/1990 | Hayashi | 422/100 |
| 4,959,050 | 9/1990 | Bobo, Jr. | 604/49 |
| 4,964,847 | 10/1990 | Prince | 604/4 |
| 4,967,753 | 11/1990 | Haase et al. | 128/662.06 |
| 5,006,309 | 4/1991 | Khalil et al. | 422/56 |
| 5,008,082 | 4/1991 | Shaw | 422/65 |
| 5,013,529 | 5/1991 | Itoh | 422/65 X |
| 5,028,017 | 7/1991 | Simmon et al. | 244/134 C |
| 5,032,362 | 7/1991 | Marsoner et al. | 422/81 |
| 5,054,650 | 10/1991 | Price | 222/1 |
| 5,059,171 | 10/1991 | Bridge et al. | 604/67 |
| 5,182,938 | 2/1993 | Merkel | 73/19.05 |
| 5,191,878 | 3/1993 | Iida et al. | 600/157 |
| 5,204,525 | 4/1993 | Hillman et al. | 250/252.1 |
| 5,257,529 | 11/1993 | Taniguchi et al. | 73/54.09 |
| 5,275,951 | 1/1994 | Chow et al. | 436/50 |
| 5,312,016 | 5/1994 | Brennar et al. | 222/55 |
| 5,365,776 | 11/1994 | Lehmann et al. | 73/54.07 |
| 5,423,743 | 6/1995 | Butterfield | 604/50 |
| 5,429,601 | 7/1995 | Conley et al. | 604/65 |
| 5,452,619 | 9/1995 | Kawanabe et al. | 73/864.01 |
| 5,463,895 | 11/1995 | Brentz | 73/61.71 |
| 5,488,854 | 2/1996 | Kawanabe et al. | 73/19.05 |
| 5,488,874 | 2/1996 | Kawanabe et al. | 73/863.01 |
| 5,499,545 | 3/1996 | Kimura et al. | 73/863.01 X |
| 5,503,036 | 4/1996 | Nguyen et al. | 73/864.34 |
| 5,540,081 | 7/1996 | Takeda et al. | 73/37 |
| 5,750,881 | 5/1998 | Dorenkott et al. | 73/864.11 X |
| 5,811,306 | 9/1998 | Kometsu | 73/864.11 X |

FOREIGN PATENT DOCUMENTS

| | | |
|---|---|---|
| 0569213 | 11/1993 | European Pat. Off. . |
| 0571100 | 11/1993 | European Pat. Off. . |
| 0682258 | 11/1995 | European Pat. Off. . |
| 0753750 | 1/1997 | European Pat. Off. . |
| 2443274 | 3/1976 | Germany . |
| 4209885 | 3/1992 | Germany . |
| 4241822 | 6/1994 | Germany . |
| 4421303 | 12/1994 | Germany . |
| 2-196963 | 8/1990 | Japan . |
| 0600419 | 3/1978 | U.S.S.R. . |
| 1515574 | 6/1978 | United Kingdom . |
| 89-10193 | 11/1989 | WIPO . |
| 9207241 | 4/1992 | WIPO . |
| 9208545 | 5/1992 | WIPO . |
| 9500829 | 1/1995 | WIPO . |

OTHER PUBLICATIONS

Voltage Discriminator–A Method And Circuit for Detecting Voltage Changes, *IBM Technical Disclosure Bulletin*, vol. 34, No. 9, Feb. 1992 pp. 374–380.

Infusion Line Model for the Detection of Infiltration, Extravsation, And Other Fluid Flow Faults, T.S. Harris, et al. *Transactions on Biomedical Engineering*, vol. 40 No. 2, Feb. 1993 pp. 15–16.

Abstract of JP 55–4117 dated Jan. 12, 1980.

Abstract of JP 58–108473 dated Jun. 28, 1983.

Abstract of JP 62–24151 dated Feb. 2, 1987.

FLUID HANDLER AND METHOD OF HANDLING A FLUID

REFERENCE TO RELATED APPLICATIONS

This application is a continuation-in-part application of Ser. No. 08/572,835, filed Dec. 14, 1995, and now U.S. Pat. No. 5,723,795, assigned to the assignee of the present case.

REFERENCE TO PROGRAM LISTING

Please refer to U.S. Pat. No. 5,723,795, assigned to the assignee of the present case, for a copy of the computer program listing referred to herein as being presented in Appendix A.

BACKGROUND OF INVENTION

Embodiments described herein relate generally to handling a fluid automatically. More specifically, the embodiments relate to moving a fluid into and out of a nozzle.

Fluid handlers or generally mechanisms for moving a fluid have many applications. One such application involves a type of machine referred to as an automated medical analyzer. These analyzers perform medical tests on a sample, such as blood, urine and the like. These tests may require mixing of the sample with a fluid. Once the sample is mixed with the fluid, a chemical reaction may take place. The chemical reaction can be used to provide a medical professional with medical information about the sample. Because the sample may have come from a human patient, the medical information about the sample may provide the medical professional with information about the patient's medical condition.

For these analyzers to operate as intended, and to give the correct medical information to the medical professional, it is desirable to mix only a specific amount of sample with a specific amount of fluid. If too much or too little sample, or if too much or too little fluid is used during the mixing process, then the chemical reaction between the sample and the fluid may not occur as desired. If this occurs, the test may give inaccurate medical information about the sample and about the patient. It may not be in the patient's best interests for a medical professional to be given inaccurate medical information. Therefore, it is desirable to provide a fluid handler which can alert an automated medical analyzer operator when the wrong amount of sample and/or fluid has been used with a particular medical test.

SUMMARY OF INVENTION

Methods of fluid handling are disclosed. According to one method, a tip of a nozzle is moved below a surface of the fluid to be handled. A pump fluidly associated with the nozzle is energized to move fluid into the nozzle. A pressure transducer fluidly associated with the nozzle is energized to monitor pressure fluidly associated with the nozzle. Pressure within the nozzle is substantially continuously monitored with the pressure transducer at least during operation of the pump. The pressure fluidly associated with the nozzle is substantially continuously monitored at a rate of about once per second, about ten times per second, about 100 times per second or about 1000 times per second. It is determined whether movement of fluid into the nozzle is intended or unintended based on the substantially continuously monitored pressure fluidly associated with the nozzle.

In another method, a tip of a nozzle is moved adjacent a container to receive fluid. A pump fluidly associated with the nozzle is energized to move fluid out of the nozzle. A pressure transducer fluidly associated with the nozzle is energized to monitor pressure fluidly associated with the nozzle. Pressure fluidly associated with the nozzle is substantially continuously monitored with the pressure transducer at least during operation of the pump. The pressure fluidly associated with the nozzle is substantially continuously monitored at a rate of about once per second, about ten times per second, about 100 times per second or about 1000 times per second. It is determined whether movement of fluid out of the nozzle is intended or unintended based on the substantially continuously monitored pressure fluidly associated with the nozzle.

In an additional method, a nozzle is moved adjacent a container for a fluid. A pump fluidly associated with the nozzle is energized to move fluid with respect to the nozzle. A pressure transducer fluidly associated with the nozzle is energized to monitor transient pressure fluidly associated with the nozzle. The transient pressure fluidly associated with the nozzle is substantially continuously monitored with the pressure transducer at least during operation of the pump. It is determined whether movement of fluid with respect to the nozzle is intended or unintended based on the substantially continuously monitored pressure fluidly associated with the nozzle.

DETAILED DESCRIPTION OF PREFERRED EMBODIMENTS

Embodiments described in detail below handle fluids. These embodiments can be used to handle, e.g. aspirate, dispense, mix, etc., any suitable fluid. While, for the sake of clarity of understanding, the embodiments are discussed with respect to their employments in a medical analytical instrument, it is to be understood that the embodiments may be used in any appropriate employment. Also, regarding the methods of handling a fluid described below, it is to be recognized that the steps of one method may be performed in any suitable order and that steps from one method may be combined with steps from another method to yield yet additional methods. To more clearly identify operation of the fluid handler 10, both intended, i.e. correctly performed, and unintended, i.e. incorrectly performed, fluid handling operations of the fluid handler 10 will be discussed. The fluid handler 10 is sufficient to detect unintended fluid handling operations due to factors such as clogs, clots, debris, bubbles, foam, etc. By detecting unintended fluid handling operations as they occur, it is possible to disregard tests involved without having to rely on the possibility of the test result itself being out of range to indicate an unintended fluid handling operation. This can also reduce the probability of operator error.

Figure 1:
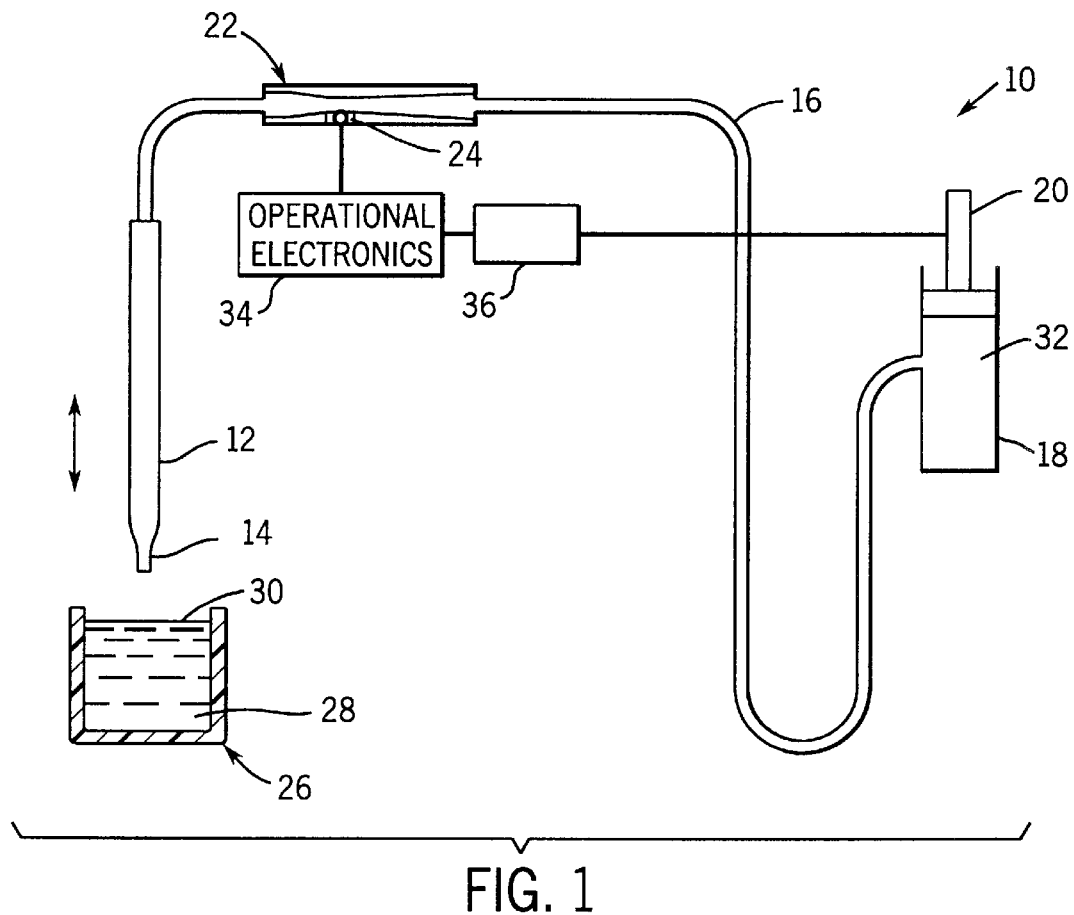
FIG. 1 is a generic diagrammatic view of a fluid handler described herein.

FIG. 1 illustrates one embodiment of a fluid handler 10. This illustrated embodiment 10 comprises a nozzle 12 having a tip 14 connected via a conduit 16 to a pump 18 operated by a prime mover 20. A pressure transducer 22 having a sensor 24 is fluidly connected with the conduit 16 between the nozzle 12 and the pump 18. The nozzle 12 may be movably supported by a suitably constructed gantry, not shown for clarity, so that the nozzle 12 may move toward and away from a container 26 retaining a fluid 28 having a fluid surface 30. The nozzle 12, the conduit 16 and the pump 18 contain a liquid 32, such as distilled water, a buffer, and the like, which facilitates aspiration and dispense of fluid 28. Thus, the pressure transducer 22 is "in line" with the liquid 32. To control and to monitor operation of the fluid handler 10, the pressure transducer 22 is electrically connected with operational electronics 34 which are, in turn, electrically connected with a controller 36. The controller 36 is electrically connected with the prime mover 20 of the pump 18 so that the pump 18 and the operational electronics 34 can operate in unison.

In one particular construction of the fluid handler 10, the nozzle 12 is a rigid aspiration probe. This probe has an inner diameter of about 0.04 inches, a length of about 7 inches, and a tip with an inner diameter of about 0.014 inches and a length of about 0.278 inches. In this construction, the conduit 16 is made of a polymer of low compliance, such as TEFZEL tubing (available from Du Pont Co., Wilmington, Del.), with an inner diameter of about 0.063 inches. If it is desirable to minimize damping of transient pressure variations, then the axial length of the conduit 16, particularly between the nozzle 12 and the pressure transducer 22, should be minimized or rendered as short as practical. However, it is to be remembered that the pressure transducer 22 may be located at any place so long as the pressure transducer 22 is able to substantially continuously monitor pressure, including but not limited to transient pressure variations, fluidly associated with the nozzle 12.

In one construction, the pressure transducer 22 may be a TransPac IV, manufactured by Abbott Laboratories, Salt Lake City, Utah. Generally, the pressure transducer 22 should be capable of sensing rapid transient pressure changes within a range of at least about −2 to about 6 psig, and particularly should have an overpressure capability to about 100 psig to enable effective washing of the nozzle 12. The pressure transducer 22 should have a fast response time, up to about 10 kHz. The pressure transducer 22 monitors pressure within the conduit 16 substantially continuously, thereby monitoring transient conduit 16 pressures, i.e. pressures fluidly associated with the nozzle 12, which allows unintended aspirations and dispenses to be indicated almost immediately. Significant transient variations in the pressure fluidly associated with the nozzle 12 may exist for a limited time period. Thus, it is desirable to monitor the pressure fluidly associated with the nozzle 12 in a substantially continuous manner. In one embodiment, the pressure within the conduit 16 is monitored at a rate of about 1000 times per second. In other embodiments, the pressure within the conduit 16 is monitored at a rate of about 100 times per second, about 10 times per second, about once per second, or any suitable rate, which may be dictated by such factors as desired sensitivity, available computer memory, etc. In any case, it is to be noted that the pressure within the conduit 16 is monitored substantially continuously so as to identify unintended fluid movements of any degree of interest. In one construction, the pump 18 is a syringe pump, such as a Cavro 3000 (Cavro Scientific Instruments Inc., Sunnyvale, Calif.). It is to be recognized that these specific constructions and others below are given for the sake of facilitating understanding.

Figure 2:
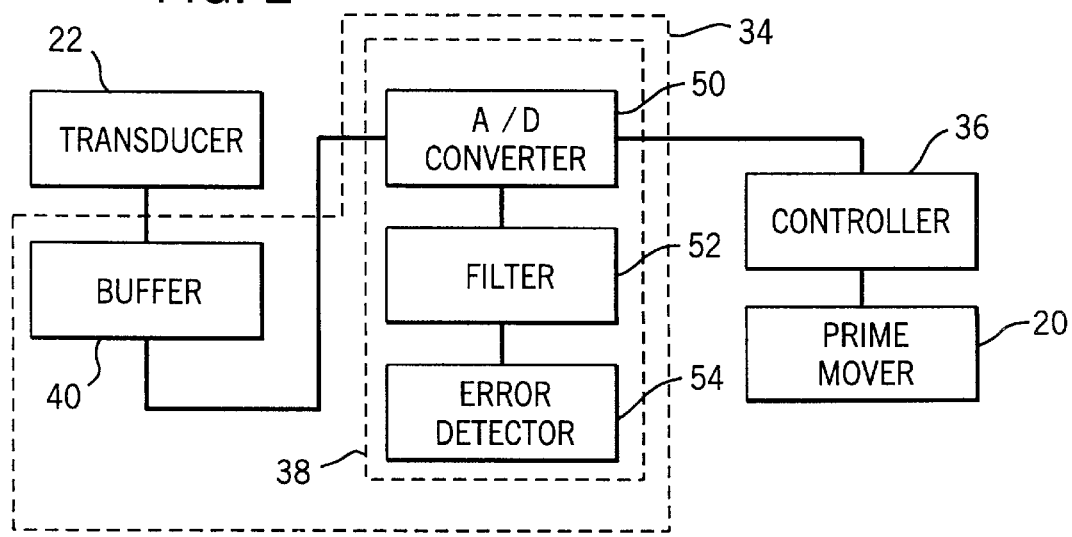
FIG. 2 is a block schematic diagram of a portion of the fluid handler shown in FIG. 1.
Figure 3:
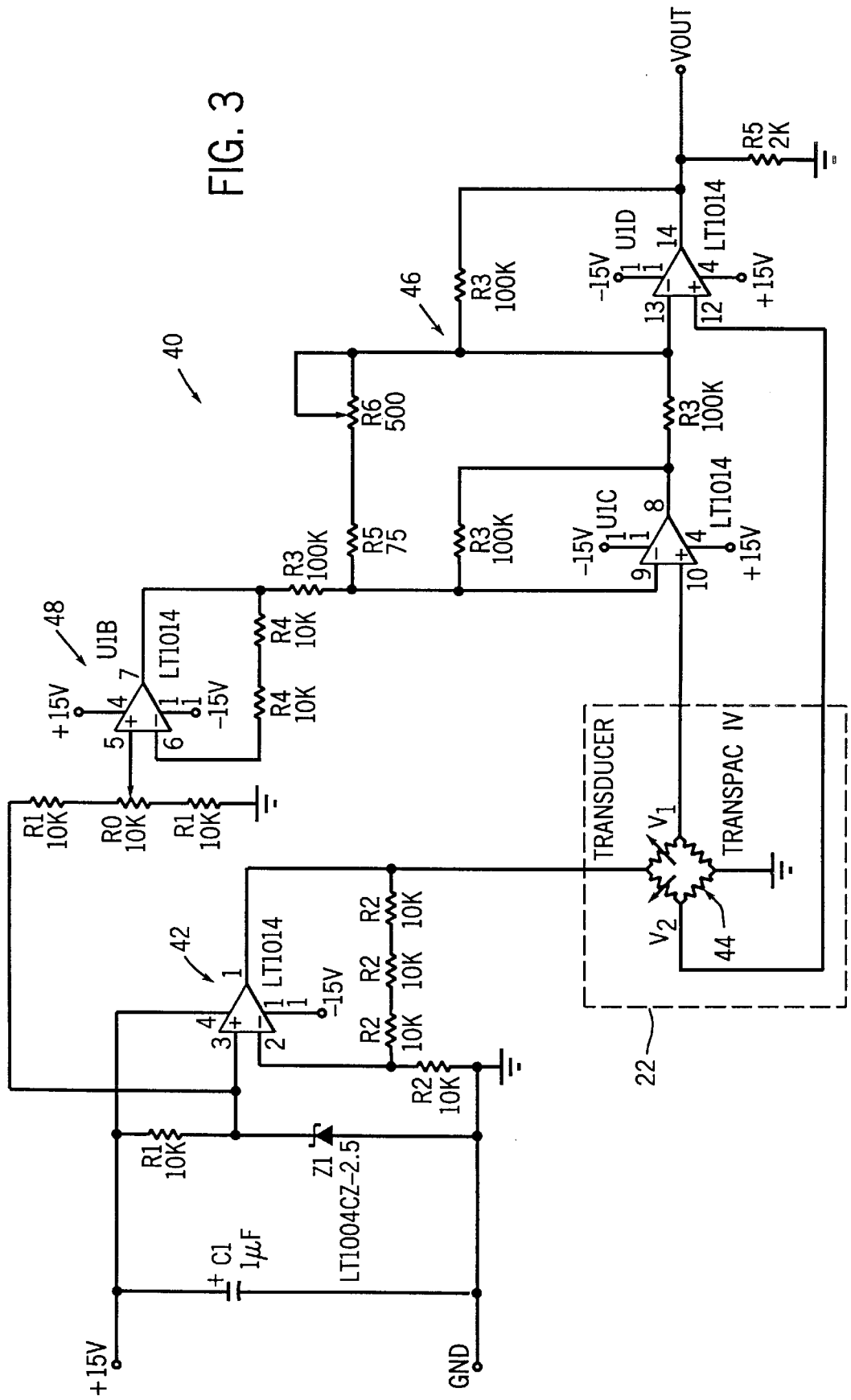
FIG. 3 is a schematic diagram of a portion of the fluid handler shown in FIG. 2.

A description of a particular construction of the operational electronics 34 follows with reference to FIGS. 2 and 3. However, it is emphasized that this is only one possible construction for controlling operation of the fluid handler 10. For instance, portions of the operational electronics 34 and/or its functions may be incorporated into a computer 38, provided in hardware or software form, etc.

As shown in FIG. 2, the pressure transducer 22 is electrically connected to an electronic buffer circuit 40 so that an electrical signal generated by the sensor 24 responsive to a pressure in the conduit 16 is transmitted to the buffer circuit 40. A detailed schematic of one embodiment of the buffer circuit 40 is illustrated in FIG. 3. The buffer circuit 40 of FIG. 3 includes a voltage source circuit 42 which supplies about 10 VDC to a bridge circuit 44 associated with the pressure transducer 22. An electrical output of the bridge circuit 44 is electrically connected to a differential amplifier circuit 46, which is also connected to an adjustable offset voltage generator circuit 48. An output of the differential amplifier circuit 46 is the output of the electronic buffer circuit 40. The output voltage of the differential amplifier circuit 46 can be expressed as:

$$V_{out} = \left( \frac{2R_3}{R_5 + R_6} + 2 \right)(V_2 - V_1) + V_A$$

The output of the differential amplifier circuit 46 is electrically connected to an analog to digital converter 50. The analog to digital converter 50 may be provided as part of the computer 38 or as part of another computer. In another construction, the analog to digital converter 50 may be substantially similar to an ATMIO-16-L9 from National Instruments of Austin, Tex.

In the illustrated embodiment, an output of the analog to digital converter 50 is electrically connected to a digital filter 52. In one embodiment, the digital filter 52 may be substantially similar to a digital lowpass filter, such as a digital Butterworth filter algorithm and the like. This algorithm may be performed by the computer 38. In a particular embodiment, the filter algorithm of the commercial software package MathCAD (available from MathSoft, Inc., Cambridge, Mass.) may be used. In other embodiments, filtering may be performed by an analog filter incorporated into the buffer circuit 40 or some other digital filter performed by the computer 38.

An output of the digital filter 52 is electrically connected to an error detector 54. The error detector 54 may be of any suitable construction, such as a software routine, a hardware configuration, an electrical circuit etc., that performs fluid handling error detection tasks as detailed below. In some embodiments, the error detector 54 may be part of the computer 38 or may be a separate signal processing device or microcontroller. The computer 38 or the error detector 54 may be electrically connected to the controller 36 to allow operation of the pump 18 to be responsive to a signal from the pressure transducer 22.

Further appreciation of the construction of the fluid handler 10 may be obtained with a discussion of the operation of the fluid handler 10. This discussion is provided for clarity of understanding.

According to one method of operation, referring to FIGS. 1 through 3, liquid 32 fills the nozzle 12, the conduit 16, the pressure transducer 22 and the pump 18. In some cases, the pump 18 may move the liquid 32 within the fluid handler 10 such that a volume, about 5 to 10 $\mu$l, of ambient air may be located within the nozzle 12 adjacent the tip 14. This volume of air may be used to separate fluid 28 aspirated from the container 26 into the nozzle 12 and the liquid 32 already present in the nozzle 12. This procedure can also be used to "stack" different fluids 28 within the nozzle 12. In essence, a first fluid 28, such as sample, is aspirated (discussed below) into the nozzle 12 and is separated from the liquid 32 by the first air volume. When a second fluid 28, such as a reagent, is aspirated into the nozzle 12, a second air volume separates the second fluid 28 from the first fluid 28. Then, the first and second fluids 28 can be dispensed from the nozzle 12 into the same of a different container 26, such as a reaction vessel. This procedure can be used to increase throughput.

To handle fluid 28, the nozzle 12 is moved by a suitable prime mover, not shown for clarity, towards the surface 30 of the fluid 28 to be handled. The nozzle 12 is moved so that the tip 14 of the nozzle 12 is offset sufficiently below the surface 30 of the fluid 28 within the container 26. An appropriate level sense mechanism, such as an R-F level sense, a capacitive level sense, a pneumatic level sense and the like, may be operatively associated with the nozzle 12 to facilitate automated detection of the surface 30 of the fluid 28. The distance of the offset between the surface 30 of the fluid 28 and the tip 14 of the nozzle 12 may vary depending upon fluid characteristics, level sense mechanism employed, ambient conditions, etc.

Once the tip 14 of the nozzle 12 is sufficiently offset below the surface 30 of the fluid 28 within the container 26, the controller 36 energizes the prime mover 20 associated with the pump 18. Substantially simultaneously, the controller 36 also energizes the pressure transducer 22. It is to be noted that, in some embodiments, the pressure transducer 22 may be energized, and thereby substantially continuously monitor pressure fluidly associated with the nozzle 12 at any time and for any time period extending between a first time prior to energizing of the prime mover 20 and a second time after completion of operation of the prime mover 20.

The pump 18 moves or aspirates a desired amount of fluid 28 from the container 26 and into the interior of the nozzle 12. As the fluid 28 passes from the container 26 into the interior of the nozzle 12, the sensor 24 of the pressure transducer 22 constantly measures pressure within the conduit 16 and detects a transient pressure change caused by flow of fluid 28 and liquid 32 within the nozzle 12 and the conduit 16 influenced by operation of the pump 18. The signals energizing the prime mover 20 sent from the controller 36 to the prime mover 20 correspond to a signal expected to be received from the sensor 24. This facilitates analysis of the signal from the sensor 24.

Responsive to the pressure sensed by the sensor 24 of the pressure transducer 22, the bridge circuit 44 generates an electrical signal. The electrical signal generated by the bridge circuit 44 is sent to the differential amplifier circuit 46 of the buffer circuit 40. The buffer circuit 40 produces an amplified electrical signal representative of an instantaneous pressure sensed by the sensor 24. The amplified electrical signal is fed into the computer 38. Once the amplified electrical signal is sent to the computer 38, the analog to digital converter 50 generates a digital signal corresponding to a voltage of the amplified electrical signal emitted by the buffer circuit 40. Thus, the digital signal is indicative of the pressure sensed by the sensor 24. The digital signal may be filtered by the digital filter 52. The filtered signal is processed by the error detector 54 which monitors a transient pressure signal to determine whether an intended aspiration has occurred. In one embodiment, the error detector 54 is enabled by a signal from the controller 36, indicating that aspiration has commenced and that the signal from the sensor 24 should be monitored for indication of errors or unintended aspirations.

The illustrated embodiment of the fluid handler 10 may also be used to monitor dispense of fluid 28 from the nozzle 12 into the container 26 or some other fluid receiver, such as a reaction vessel and the like. Substantially similarly to the above-described steps, a fluid 28 dispense is initiated by operation of the pump 18. The error detector 54 is enabled by the controller 36 substantially simultaneously with the pump 18. The error detector 54 monitors the signal, which is indicative of the pressure sensed by the sensor 24, sent by the sensor 24 and processed by the operational electronics 34 to determine whether an intended dispense has occurred.

Several methods exist for using the signal, indicative of pressure sensed by the sensor 24, sent from the sensor 24 to determine whether an intended aspiration and/or dispense has occurred based on transient pressure signals sent by the sensor 24. Some of these methods are described in the following examples. It is to be noted that these examples are provided for clarity of understanding.

In the examples, data were collected using an embodiment of the fluid handler 10 which is substantially similar to that described above. Fluid 28 volumes of about 50 $\mu$l were aspirated into the nozzle 12, with fluid 28 flow accelerated at a substantially constant rate of about 1563 $\mu$l/sec/sec until steady state flow rate of about 83 $\mu$l/sec was reached. Flow deceleration was also substantially constant at about 1563 $\mu$l/sec/sec. Dispenses of about 40 $\mu$l were also measured, with a steady flow rate of about 391 $\mu$l/sec and flow acceleration and deceleration rates of about 26,040 $\mu$l/sec/sec. The operational electronics 34 were adjusted (gain, threshold, etc.) so that an electrical signal presented to the analog to digital converter 50 is about 0 volts prior to aspiration and does not saturate the operational electronics 34 during an intended aspirate/dispense cycle, which comprises aspiration of the desired amount of fluid 28 into the nozzle 12 and dispense of a desired amount of fluid 28 from the nozzle 12. A common gain of the operational electronics 34 is about 9.6 V/psi. A representation of MathCAD software used to collect and to analyze the data in these examples is presented in Appendix A. The following examples use parameters defined in Appendix A, section 1.

EXAMPLE 1

Intended Aspiration and Dispense Profiles

Figure 4A:
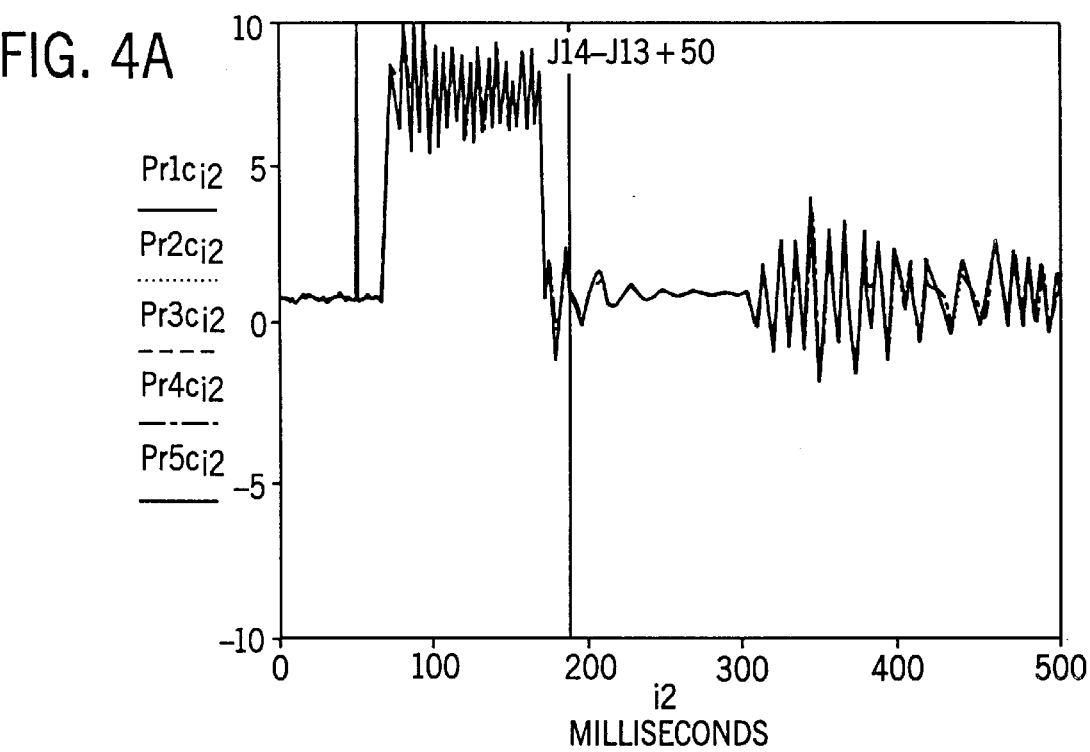
FIGS. 4A and 4B display data obtained during intended operation of the fluid handler.
Figure 4B:
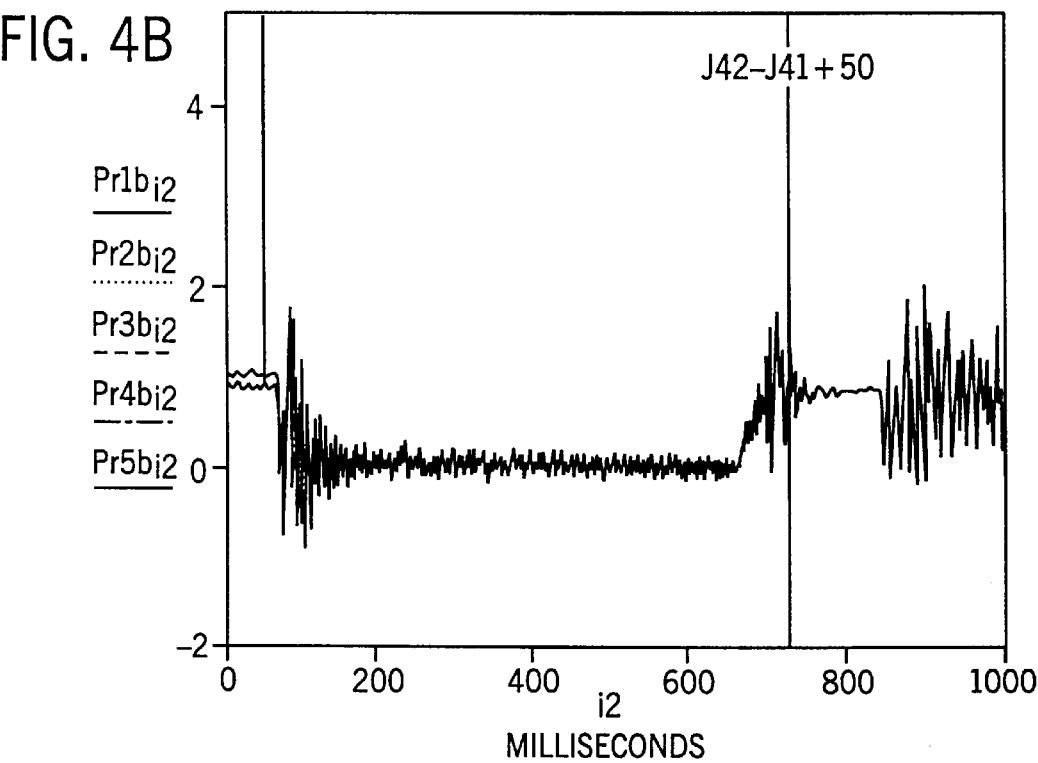

About 50 $\mu$l aspiration and about 40 $\mu$l dispense of pig serum were performed with the flow parameters as listed above. The analog pressure signal from the sensor 24 was sampled substantially continuously at a rate of about 1000 samples/second and stored as unfiltered numerical data representing the instantaneous pressure profiles sensed by the sensor 24 during both aspiration and dispense of fluid 28. Other sampling rates are also possible. The results of 5 repetitions of this experiment are presented in FIG. 4A (5 aspirations) and FIG. 4B (5 dispenses). These Figures demonstrate repeatability of the pressure sensing method. The pressure spikes immediately preceding and following the aspiration and dispense were artificially imposed on the data to facilitate extraction and display of the pressures during actual aspiration and dispense. A representation of Math-CAD software used to extract the pressures during aspiration and dispense is found in Appendix A, section 2. From this, it is apparent that an instantaneous pressure profile derived from data obtained by the sensor 24 can be compared to a predetermined pressure profile to conclude whether the fluid handling operation involved was intended or unintended.

EXAMPLE 2

Unintended Aspiration and Dispense

Figure 5A:
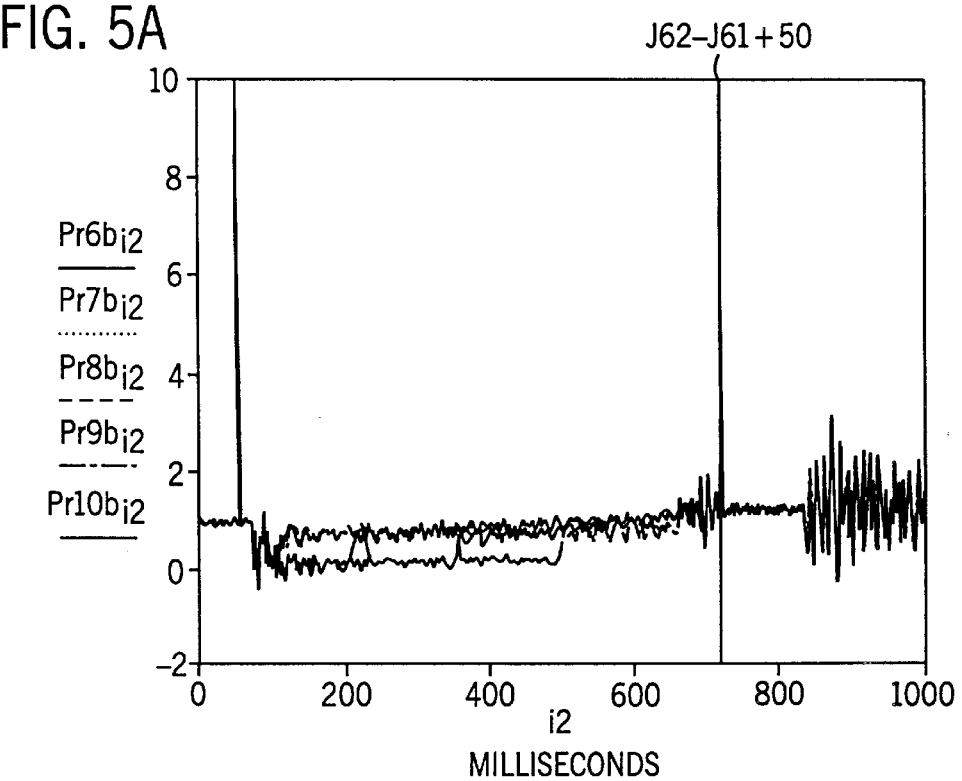
FIGS. 5A and 5B display data obtained during unintended operation of the fluid handler.
Figure 5B:
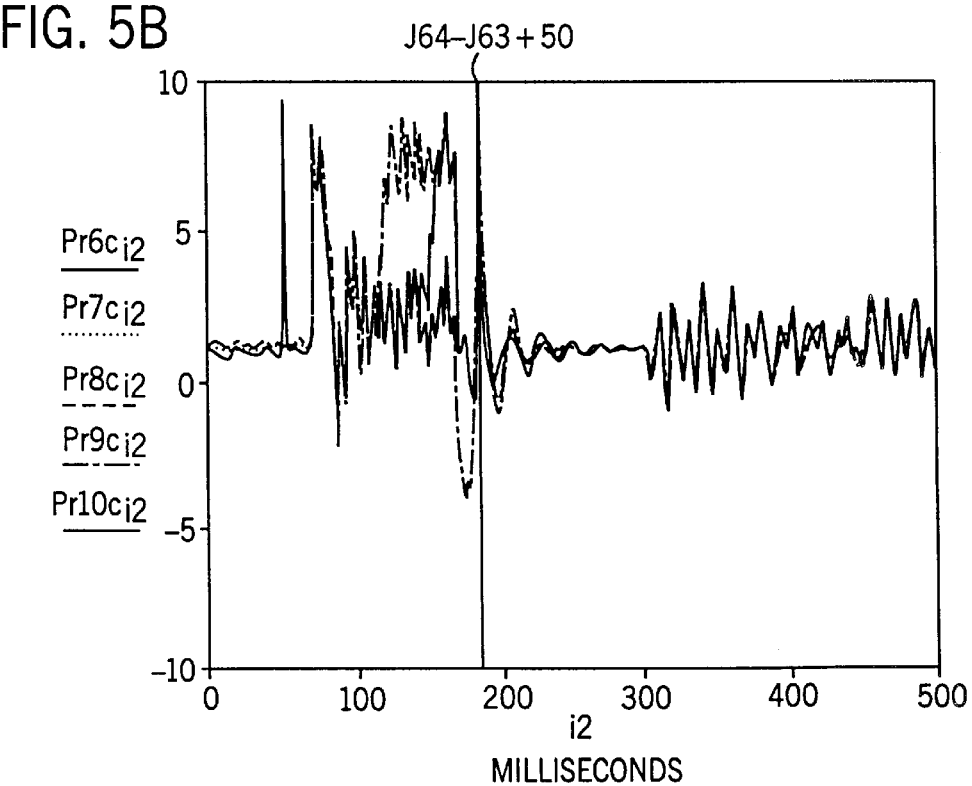

Interrupted aspiration of pig serum was performed by removing the container 26 from the nozzle 12 during an about 50 μl aspiration, resulting in partial aspiration of air. The dispense portion of the aspirate/dispense cycle consequently also included partial dispense of air. Instantaneous pressure profiles of 5 unintended aspirations and dispenses were produced as in Example 1 and are illustrated in FIG. 5A (5 aspirations) and FIG. 5B (5 dispenses). Varying amounts of air were aspired during the unintended aspirations. A representation of the MathCAD software used to extract the pressures during the unintended aspiration and dispense is found in Appendix A, section 3.

EXAMPLE 3

Digital Filtering of Pressure Profiles

Figure 6A:
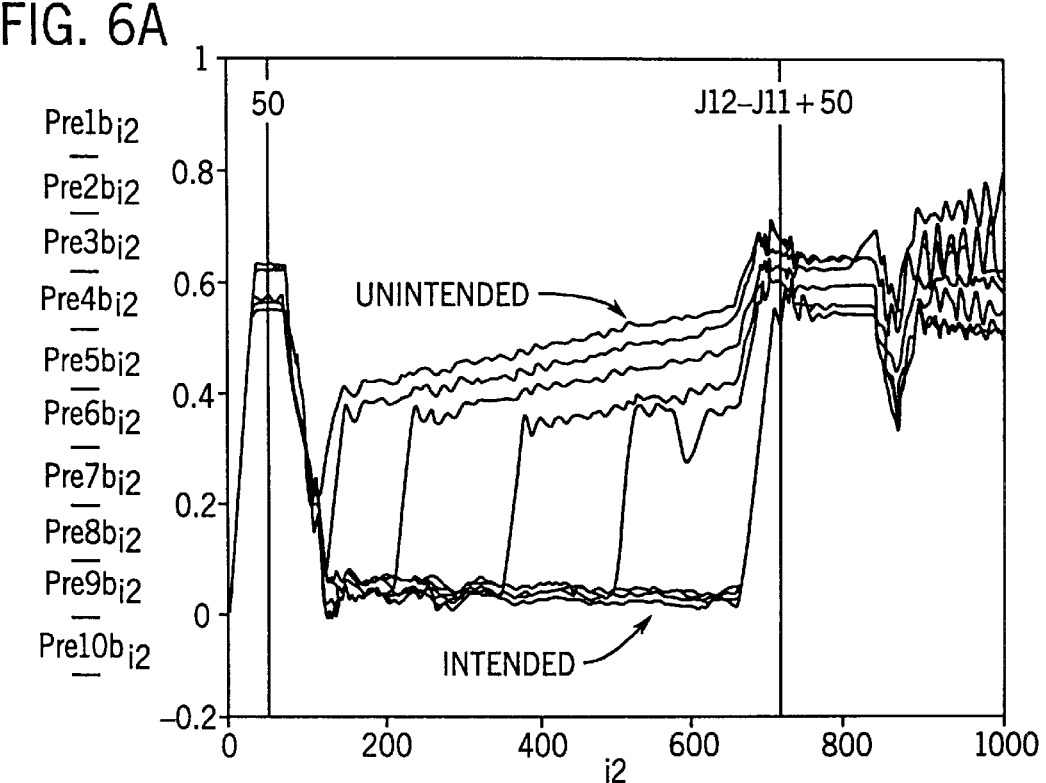
FIGS. 6A and 6B display filtered data obtained during operation of the fluid handler.
Figure 6B:
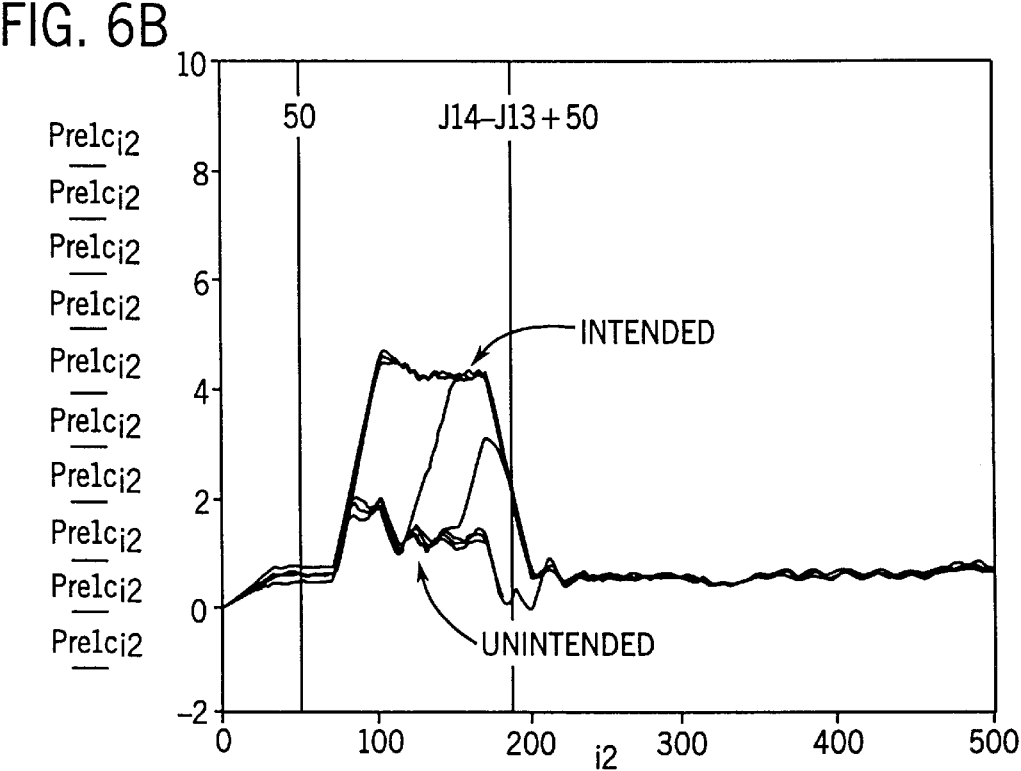

The pressure profile data acquired as described in examples 1 and 2 was filtered with a MathCAD digital Butterworth filter described above. This is a 31 coefficient digital lowpass filter with a cutoff frequency of about 0.01 times the sampling frequency (or about 10 Hz). A representation of the MathCAD software used to execute this filtering is found in Appendix A, section 4. The results of this filtering are illustrated in FIG. 6A (5 intended and 5 unintended aspirations) and FIG. 6B (5 intended and 5 unintended dispenses). The unintended aspirations and dispenses are clearly distinguishable from the intended aspiration and dispense profiles.

EXAMPLE 4

Error Detection by Integration

Intended and unintended filtered and unfiltered pressure profile data was integrated as an exemplary error detection method. The integration was mathematically performed with MathCAD software (represented in Appendix A, sections 2, 3, and 5). The results of the integration are presented in Table 1. The integration results for the intended aspirations and dispenses are statistically distinguishable from those of the unintended aspirations and dispenses. This method is, however, sensitive to fluid viscosity (which may range from about 1 to about 14 centipoise) and accordingly is less desirable for small aspiration and dispense volumes (on the order of about 10 μl).

EXAMPLE 5

Error Detection by Mean Pressure Difference

Five consecutive data points were sampled from each of the filtered intended and unintended aspiration pressure profiles immediately prior to syringe deceleration, so that they represent pressure sensed by the sensor 24 during steady-state. Five consecutive data points were also sampled following completion of aspiration. The difference between the mean pressure during steady state aspiration and the mean pressure following completion of the aspiration was calculated and compared to a tolerance band. In this example, executed by the software represented in Appendix A, section 6, the tolerance band was from about 0.35 to about 0.55. As shown in Table 2, the intended aspirations yielded mean pressure differences within the tolerance band, while the unintended aspirations yielded pressure differences outside the band.

EXAMPLE 6

Error Detection by Variation of Pressure Difference from Mean

Data points from each of the filtered intended and unintended aspiration pressure profiles that fell within the steady state aspiration region were used to calculate the instantaneous difference between the pressure sensed by the sensor 24 at any time and the pressure sensed following completion of the aspiration. Each of these values was compared to the mean difference between the pressure during steady state aspiration and the pressure following aspiration (calculated as in Example 5). The number of times that the instantaneous pressure difference differed from the mean pressure difference by more than a specified tolerance was counted. In the case of the software represented in Appendix A, section 7, the tolerance band was about 0.1 on either side of the mean difference. As shown in Table 3, the intended aspiration profiles had uniformly zero deviations outside of the tolerance band, while the unintended aspirations had numerous such deviations.

The error detection methods presented in Examples 4 through 6 are just four of the many possible methods to detect unintended aspirations and dispenses from the pressure profiles measured by the sensor 24. In some embodiments, several error detection methods may be combined. The Examples demonstrate that the pressure data collected by embodiments of the fluid handler 10 may be used in an aspiration and dispense error detection method.

The pressure profiles of intended and unintended aspirations and dispenses are directly affected by the acceleration and deceleration profiles of the pump 18. For instance, a uniform ramp acceleration and deceleration of the pump 18 will result in pressure values that do not reach steady state. It is possible to modify the acceleration and deceleration profiles of the pump 18 to yield intended and unintended aspiration and dispense pressure profiles that may be more easily or reliably distinguished by these or other error detection schemes. In other embodiments, feedback from elements, other than the pressure transducer 22, of the fluid handler 10, such as movement of the pump 18, fluid surface 30 level sense information, etc., alone or in combination with each other or with the pressure transducer 22 information, can be used to provide an indication of intended or unintended fluid handling operations.

TABLE 1

| Error Detection by Integration of Pressure | | | |
|---|---|---|---|
| Integrated Pressure Values | | | |
| Aspiration | | Dispense | |
| Intended | Unintended | Intended | Unintended |
| Filtered | | | |
| 1268 | 1020 | 438 | 145 |
| 1287 | 1047 | 448 | 154 |
| 1282 | 1212 | 443 | 321 |
| 1272 | 1099 | 442 | 167 |
| 1285 | 1166 | 439 | 225 |

TABLE 1-continued

Error Detection by Integration of Pressure

| | Integrated Pressure Values | | |
|---|---|---|---|
| Aspiration | | Dispense | |
| Intended | Unintended | Intended | Unintended |
| Unfiltered | | | |
| 1212 | 787 | 774 | 238 |
| 1241 | 829 | 787 | 253 |
| 1233 | 1114 | 778 | 568 |
| 1216 | 919 | 772 | 266 |
| 1236 | 1033 | 771 | 399 |

TABLE 2

Error Detection by Mean Pressure Difference
Mean pressure difference

| Intended | | Unintended | |
|---|---|---|---|
| 0.496 | Within tolerance | 0.141 | Outside tolerance |
| 0.528 | Within tolerance | 0.169 | Outside tolerance |
| 0.517 | Within tolerance | 0.225 | Outside tolerance |
| 0.501 | Within tolerance | 0.185 | Outside tolerance |
| 0.509 | Within tolerance | 0.230 | Outside tolerance |

TABLE 3

Error Detection by Variation of Pressure Difference from Mean
Number of points outside tolerance band

| Intended | Unintended |
|---|---|
| 0 | 78 |
| 0 | 82 |
| 0 | 378 |
| 0 | 110 |
| 0 | 233 |

What is claimed is:

1. A method of handling a fluid, the method comprising the steps of:
   (a) moving a tip of a nozzle below a surface of the fluid to be handled;
   (b) energizing a pump fluidly associated with the nozzle to move fluid into the nozzle;
   (c) energizing a pressure transducer fluidly associated with the nozzle to monitor pressure fluidly associated with the nozzle;
   (d) substantially continuously monitoring pressure fluidly associated with the nozzle with the pressure transducer at least during operation of the pump, wherein the monitoring step (d) comprises monitoring pressure fluidly associated with the nozzle at a rate of about ten times per second; and
   (e) determining whether movement of fluid into the nozzle is intended or unintended based on the substantially continuously monitored pressure fluidly associated with the nozzle.

2. A method of handling a fluid, the method comprising the steps of:
   (a) moving a tip of a nozzle adjacent a container to receive the fluid;
   (b) energizing a pump fluidly associated with the nozzle to move fluid out of the nozzle;
   (c) energizing a pressure transducer fluidly associated with the nozzle to monitor pressure fluidly associated with the nozzle;
   (d) substantially continuously monitoring pressure fluidly associated with the nozzle with the pressure transducer during operation of the pump, wherein the monitoring step (d) comprises monitoring pressure fluidly associated with the nozzle at a rate of about ten times per second; and
   (e) determining whether movement of fluid out of the nozzle is intended or unintended based on the substantially continuously monitored pressure fluidly associated with the nozzle.

3. A method of handling a fluid, the method comprising the steps of:
   (a) moving a tip of a nozzle below a surface of the fluid to be handled;
   (b) energizing a pump fluidly associated with the nozzle to move fluid into the nozzle;
   (c) energizing a pressure transducer fluidly associated with the nozzle to monitor pressure fluidly associated with the nozzle;
   (d) substantially continuously monitoring pressure fluidly associated with the nozzle with the pressure transducer at least during operation of the pump, wherein the monitoring step (d) comprises monitoring pressure fluidly associated with the nozzle at a rate of about 100 times per second; and
   (e) determining whether movement of fluid into the nozzle is intended or unintended based on the substantially continuously monitored pressure fluidly associated with the nozzle.

4. A method of handling a fluid, the method comprising the steps of:
   (a) moving a tip of a nozzle adjacent a container to receive the fluid;
   (b) energizing a pump fluidly associated with the nozzle to move fluid out of the nozzle;
   (c) energizing a pressure transducer fluidly associated with the nozzle to monitor pressure fluidly associated with the nozzle;
   (d) substantially continuously monitoring pressure fluidly associated with the nozzle with the pressure transducer during operation of the pump, wherein the monitoring step (d) comprises monitoring pressure fluidly associated with the nozzle at a rate of about 100 times per second; and
   (e) determining whether movement of fluid out of the nozzle is intended or unintended based on the substantially continuously monitored pressure fluidly associated with the nozzle.

* * * * *